(12) United States Patent
Hendrick et al.

(10) Patent No.: US 12,310,684 B2
(45) Date of Patent: May 27, 2025

(54) INSERTION METHODS FOR ROBOTIC SURGICAL DEVICES

(71) Applicant: Virtuoso Surgical, Inc., Nashville, TN (US)

(72) Inventors: Richard Hendrick, Nashville, TN (US); Neal Dillon, Nashville, TN (US); Evan Blum, Nashville, TN (US)

(73) Assignee: Virtuoso Surgical, Inc., Nashville, TN (US)

( * ) Notice: Subject to any disclaimer, the term of this patent is extended or adjusted under 35 U.S.C. 154(b) by 0 days.

(21) Appl. No.: 18/130,855

(22) Filed: Apr. 4, 2023

(65) Prior Publication Data
US 2023/0240769 A1    Aug. 3, 2023

Related U.S. Application Data

(63) Continuation of application No. 16/446,202, filed on Jun. 19, 2019, now Pat. No. 11,628,020.

(51) Int. Cl.
*A61B 1/018*    (2006.01)
*A61B 1/00*    (2006.01)
(Continued)

(52) U.S. Cl.
CPC .......... *A61B 34/30* (2016.02); *A61B 1/00087* (2013.01); *A61B 1/00098* (2013.01);
(Continued)

(58) Field of Classification Search
CPC ............ A61B 1/00133; A61B 1/00154; A61B 1/0016; A61B 1/01; A61B 1/018;
(Continued)

(56) References Cited

U.S. PATENT DOCUMENTS

2003/0004400 A1\*    1/2003    Smith ................... A61B 1/018
                                                    600/153
2008/0287961 A1\*    11/2008   Miyamoto ............. A61B 1/018
                                                    606/127
2015/0080907 A1      3/2015    Herrell et al.

FOREIGN PATENT DOCUMENTS

JP        2002500530 A    1/2002
JP        2012502681 A    2/2012
(Continued)

OTHER PUBLICATIONS

Office Action cited in related Japanese Application Serial No. 2021-576267 dated Apr. 17, 2024.

*Primary Examiner* — Aaron B Fairchild
(74) *Attorney, Agent, or Firm* — Holland & Knight LLP; Matthew C. Cox

(57) ABSTRACT

An insertable robot for minimally invasive surgery includes a tube array having a guide tube housed within a straightening tube. The guide tube includes a curved working end. The guide tube may be axially translated and rotated relative to the straightening tube such that the curved working end is constrained inside the straightening tube, causing the curved working end to achieve a smaller dimension. The tube array is inserted into a working channel on an endoscope, resectoscope or trocar. Once the tube array is inserted, the curved working end of the guide tube is translated forward beyond the distal end of the working channel, allowing the curved working end to return to its pre-formed shape. A surgical tool is inserted through the guide tube for an operation. The straightening tube allows the guide tube curved working end to be temporarily straightened during insertion and removal of the tube array.

8 Claims, 15 Drawing Sheets

(51) Int. Cl.
*A61B 34/30* (2016.01)
*A61B 1/313* (2006.01)
*A61B 17/00* (2006.01)
*A61B 17/221* (2006.01)
*A61B 17/29* (2006.01)
*A61B 17/32* (2006.01)
*A61B 18/24* (2006.01)
*A61M 25/00* (2006.01)
*A61M 25/01* (2006.01)
*A61M 25/06* (2006.01)

(52) U.S. Cl.
CPC .......... *A61B 1/00133* (2013.01); *A61B 1/018* (2013.01); *A61B 1/313* (2013.01); *A61B 2017/0034* (2013.01); *A61B 17/221* (2013.01); *A61B 17/29* (2013.01); *A61B 17/320016* (2013.01); *A61B 18/24* (2013.01); *A61B 2034/301* (2016.02); *A61M 2025/0004* (2013.01); *A61M 25/0116* (2013.01); *A61M 25/0662* (2013.01)

(58) Field of Classification Search
CPC ..... A61B 17/34; A61B 17/3417; A61B 34/30; A61B 2034/301; A61B 1/00087; A61B 1/00098; A61M 25/0662; A61M 25/0102; A61M 25/0105; A61M 2025/0681
See application file for complete search history.

(56) References Cited

FOREIGN PATENT DOCUMENTS

JP  2012513277 A  6/2012
JP  2017531482 A  10/2017

\* cited by examiner

INSERTION METHODS FOR ROBOTIC SURGICAL DEVICES

CROSS-REFERENCES TO RELATED APPLICATIONS

This application is a continuation of, and claims benefit of and priority to, U.S. patent application Ser. No. 16/446,202 filed Jun. 19, 2019 entitled INSERTABLE ROBOT FOR MINIMALLY INVASIVE SURGERY, which is hereby incorporated by reference in its entirety.

STATEMENT REGARDING FEDERALLY SPONSORED RESEARCH OR DEVELOPMENT

This invention was made with government support under R44EBO24423 awarded by the National Institutes of Health. The government has certain rights in the invention.

BACKGROUND

The present invention relates to surgical instruments and associated methods for performing surgery. More particularly, the present invention relates to tools and methods for minimally invasive surgery using concentric tube robot assemblies.

Minimally invasive surgery using electromechanical robots is a developing field of medicine. Conventional devices for performing minimally invasive surgery, such as endoscopes and resectoscopes, generally include a distal tip that is inserted through an incision in a patient's body or a natural orifice in a patient's body. The distal tip includes an optical lens which allows a surgeon to see a field of view proximate to the distal tip when placed inside the body. The endoscope will typically have a camera attached to it to display the field of view on an operating room monitor. In some applications the endoscope includes a camera installed on the distal tip of the endoscope. The device also includes a working channel extending through the device. One or more elongated surgical tools may be inserted through the working channel. A tool such as a cutting device, a basket or a laser optic may be included on the surgical tool. The distal end of the surgical tool protrudes from the distal tip of the device, thereby allowing the surgeon to visually observe operation of the tool inside the patient's body during an operation.

Conventional surgical tools for use through the narrow working channel of an endoscope or resectoscope are generally limited in size, and are particularly limited in the maximum effective outer diameter. Because such tools must be passed through the working channel to reach the surgical site inside the body, the tools must be small enough in outer diameter to be inserted axially into the bore of a working channel in an endoscope or resectoscope. The working channel diameter in an endoscope or resectoscope is generally in the range of about one to twenty millimeters, but the devices may have different inner diameters outside of this range depending on the application. Thus, a surgical tool to be inserted through the working channel must include a similar, or a smaller, effective outer diameter to be smoothly inserted through the channel to reach the surgical site.

During a surgical procedure, it may become necessary to change a surgical tool. For example, a laser cutting fiber may need to be removed from the endoscope or resectoscope via the working channel, and a mechanical manipulator may need to be inserted through the working channel. Manipulators allow a surgeon to move the distal end of the surgical tool protruding from the distal tip of the endoscope without actually moving the endoscope. This may reduce trauma on the patient in some applications.

When a surgical tool is changed during a procedure, a first tool may be slid axially out of the working channel in a direction away from the patient, and a second tool may be slid axially into the working channel, or inserted into the working channel, in a direction toward the patient. The second tool is inserted until the distal end of the working tool is in a position to advance toward the surgical site. However, if the first or second surgical tool has a highly curved distal end, or a distal end with a large expanded profile, the second tool may not properly fit into the working channel. Thus, it may be difficult or impossible to insert the surgical tool with a curved or large profile tip into the working channel toward the patient.

What is needed then are improvements in devices and methods for performing robotic surgery.

BRIEF SUMMARY

The present invention relates generally to devices and methods for performing minimally invasive surgery. In some embodiments, the present invention includes a surgical robot apparatus including a guide tube with a curved working end housed inside a straightening tube, wherein the straightening tube at least partially straightens the curved working end of the guide tube such that the guide tube and straightening tube may be inserted simultaneously as a combined assembly through the small diameter working channel of the shaft on an endoscope, resectoscope or trocar. In various embodiments, the assembly may include additional tubes, such as an inner tube passing through the guide tube in addition to the surgical tool.

Following insertion of the guide tube and straightening tube into the working channel, the guide tube may be axially translated through the straightening tube toward a patient's body allowing the curved working end to extend from the distal end of the straightening tube and assume its naturally biased curved orientation. A surgical tool such as a laser optic, cutting tool, forceps, basket or other instrument is passed axially through the guide tube extending from the distal tip of the guide tube. The curvature of the guide tube allows a surgeon improved range of motion for the surgical tool inside the patient's body, when compared with traditional straight surgical tools. The guide tube is coupled to a transmission that allows the guide tube to be translated or rotated during a procedure to steer the surgical tool to desired tissue.

In some embodiments, the present invention includes a concentric tube robot apparatus for performing minimally invasive surgery. The apparatus includes a tube array with a guide tube and a straightening tube. The guide tube includes a curved working end. The guide tube may be translated and rotated relative to the straightening tube such that the curved working end is housed inside and constrained by the straightening tube, thereby allowing the tube array to be inserted into a narrow working channel of an endoscope, resectoscope or trocar. A transmission is also coupled to the tube array in some embodiments, providing an interchangeable cartridge configuration that can be installed or removed as a complete unit on a surgical robot during a procedure.

One objective of the present disclosure is to provide a surgical robot apparatus that allows a user to change surgical tools during surgery without removing the endoscope, resectoscope or trocar shaft from the patient's body.

Another objective of the present disclosure is to provide a surgical robot apparatus that allows a guide tube with a highly curved working end to be inserted axially through a narrow working channel on an endoscope, resectoscope or trocar.

A further objective of the present disclosure is to provide a surgical robot apparatus that includes a modular tube array with an integrated surgical tool that can be quickly changed during a surgical procedure by sliding the tube array into or out of a longitudinal straight or slightly curved working channel on a stationary endoscope, resectoscope or trocar.

Numerous other objects, features and advantages of the present invention will be readily apparent to those skilled in the art upon a reading of the following disclosure when taken in conjunction with the accompanying drawings and the claims.

DETAILED DESCRIPTION

Figure 1:
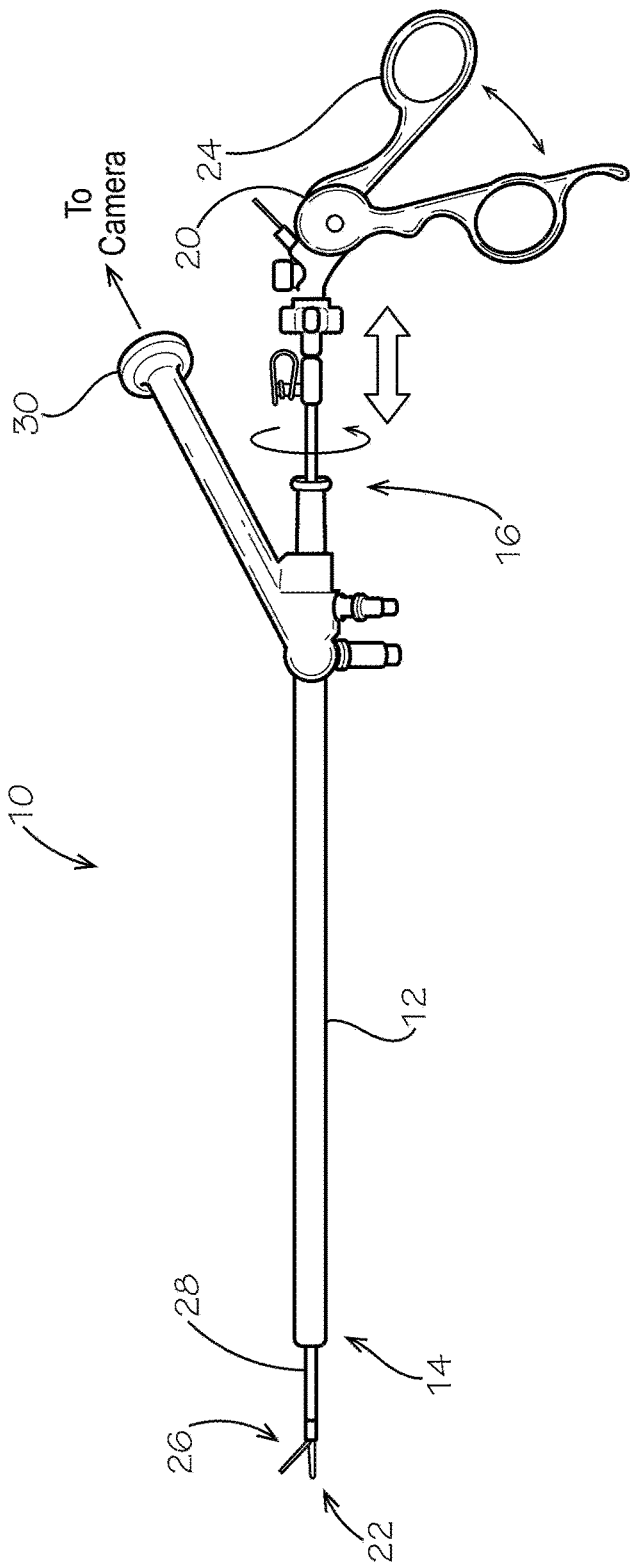
FIG. 1 illustrates a perspective view of a prior art embodiment of an endoscope including a surgical tool with an end effector protruding from the distal tip.

Referring now to the drawings, various views of embodiments of devices and methods for performing minimally invasive surgery are illustrated. In the drawings, not all reference numbers are included in each drawing, for the sake of clarity. The devices shown in the illustrations are not intended to illustrate all possible embodiments of the claimed invention, but are rather included as examples. A person of skill in the art will understand the devices and methods of the claimed invention may include different configurations and orientations not shown in the figures.

The present disclosure provides an insertable concentric tube assembly for minimally invasive surgery. During conventional minimally invasive surgery, a surgical instrument such as an endoscope, resectoscope or trocar includes a distal tip inserted into a patient's body through a small incision. A surgical tool including an end effector such as a cutting tool, probe, forceps, basket, laser fiber or other surgical tool protrudes from the distal tip for performing an operation on patient tissue. An optical lens positioned proximate the distal tip allows a surgeon to visually observe the surgical tool in vivo during the operation.

An example of a conventional endoscope device 10 for performing minimally invasive surgery is shown in FIG. 1. The device 10 includes a longitudinal shaft 12 having a distal end 14 and a proximal end 16. The longitudinal shaft 12 includes a hollow interior allowing the passage of one or more surgical instruments 20. Surgical instrument 20 includes a surgical tool with an end effector 22, such as a cutting tool or forceps, disposed on the distal tool end 26 as shown in FIG. 1. The surgical instrument 20 includes a tool actuator 24 on one end and a tool shaft 28 extending from the tool actuator. The tool shaft 28 is inserted into the longitudinal shaft 12 of the endoscope device 10 such that the distal tool end 26 and the end effector 22 protrude from an opening at the distal end 14 of the of the device 10.

During surgery, the distal end 14 of the device 10, together with the distal tool end 26 and end effector 22 are inserted into a patient's body. The tool actuator 24 may then be manipulated to activate the end effector 22, for example to perform a cutting operation to remove patient tissue from within the body. During this procedure, the surgical tool 20 may be manipulated relative to the device 10 by moving the surgical tool axially such that the tool shaft translates within the longitudinal shaft 12, thereby moving the longitudinal position of the end effector 22 relative to the distal end 14 of the device 10. Additionally, the surgical instrument 20 may be rotated angularly about the longitudinal axis of the shaft 12, thereby causing the end effector 22 to rotate relative to the distal end 14 of the device 10.

During minimally invasive surgery, it is beneficial for a surgeon to be able to visually observe the position of the end effector 22 relative to the tissue undergoing operation. As shown in FIG. 1, endoscope device 10 in some embodiments includes an optical port 30 for a camera or optic to be inserted into the device 10 such that the camera or optic extends through the interior of the longitudinal shaft 12 alongside the tool shaft 28.

Figure 2A:
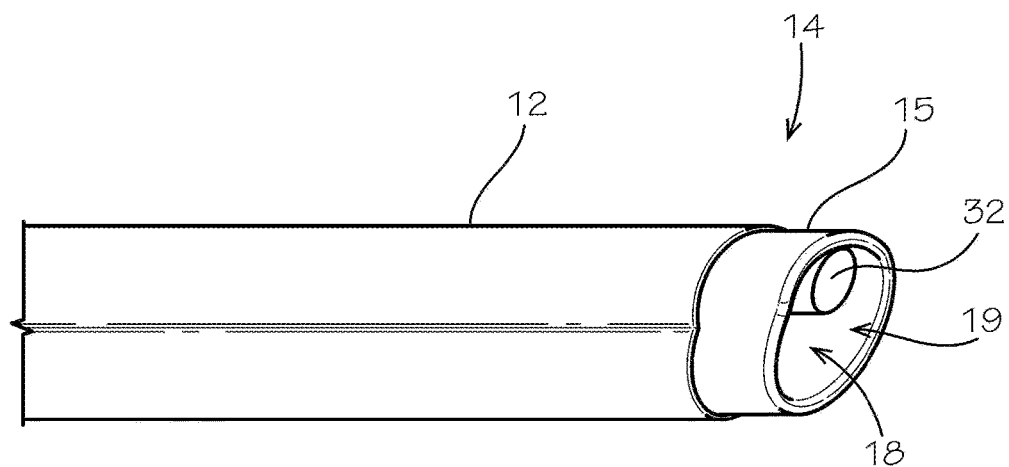
FIG. 2A illustrates a detail perspective view of a prior art embodiment of an endoscope distal tip with a lens and a working channel opening below the lens.
Figure 2B:
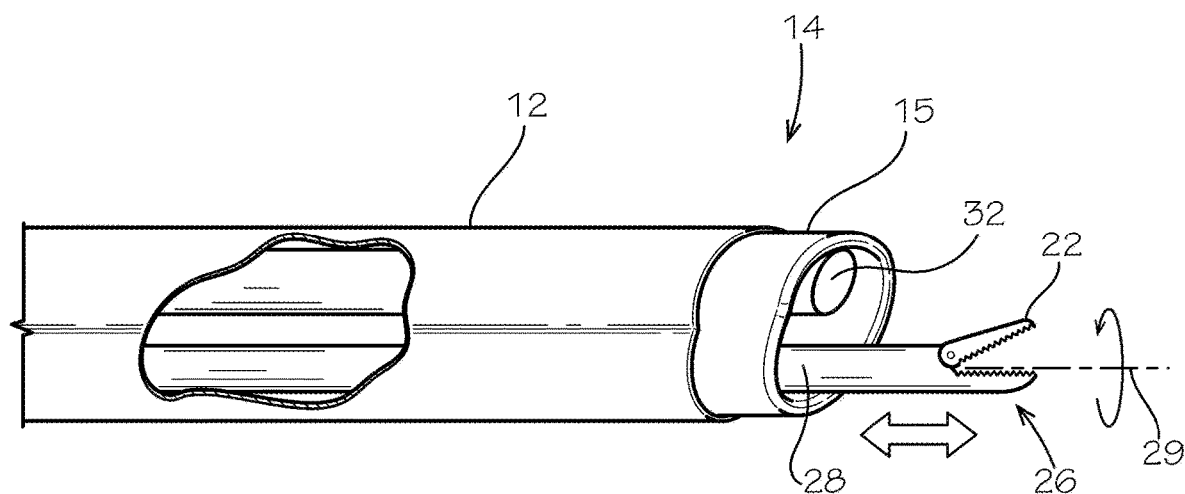
FIG. 2B illustrates a detail cutaway perspective view of the prior art embodiment of an endoscope of FIG. 2A with a surgical tool and end effector protruding from the distal tip.

An example of a distal end 14 of a tubular, hollow longitudinal shaft 12 of a conventional endoscope, resectoscope or trocar is shown in FIGS. 2A and 2B. The longitudinal shaft 12 includes an end opening 19 at the distal end 14. A hood 15 surrounds the end opening 19 in some embodiments. A working channel 18 is defined through the hollow interior of the longitudinal shaft 12, and one or more tools may be passed through the working channel 18 toward the end opening 19. An optical lens 32 is positioned proximate the end opening 19 in some embodiments. The optical lens 32 is coupled to an optical fiber 34 to provide imaging capabilities to a surgeon. The optical fiber 34 extends through the working channel 18 of the longitudinal shaft 12.

Also shown in FIGS. 2A and 2B, a conventional tool shaft 28 extends through the working channel 18 toward the end opening 19 at the distal end 14 of the longitudinal shaft 12. The tool shaft 28 is part of a surgical instrument that may be manipulated manually by a surgeon or teleoperated by a surgeon using a robotic interface to actuate end effector 22 and to move distal tool end 26 axially or angularly relative to tool shaft axis 29. During a procedure, tool shaft 28 may be axially translated in and out of end opening 19 manually or using a mechanized transmission linkage coupled to the tool shaft 28. Additionally, during a procedure, tool shaft 28 may also be rotated angularly about tool shaft axis 29 manually or using a transmission linkage coupled to the tool shaft 28.

Figure 3:
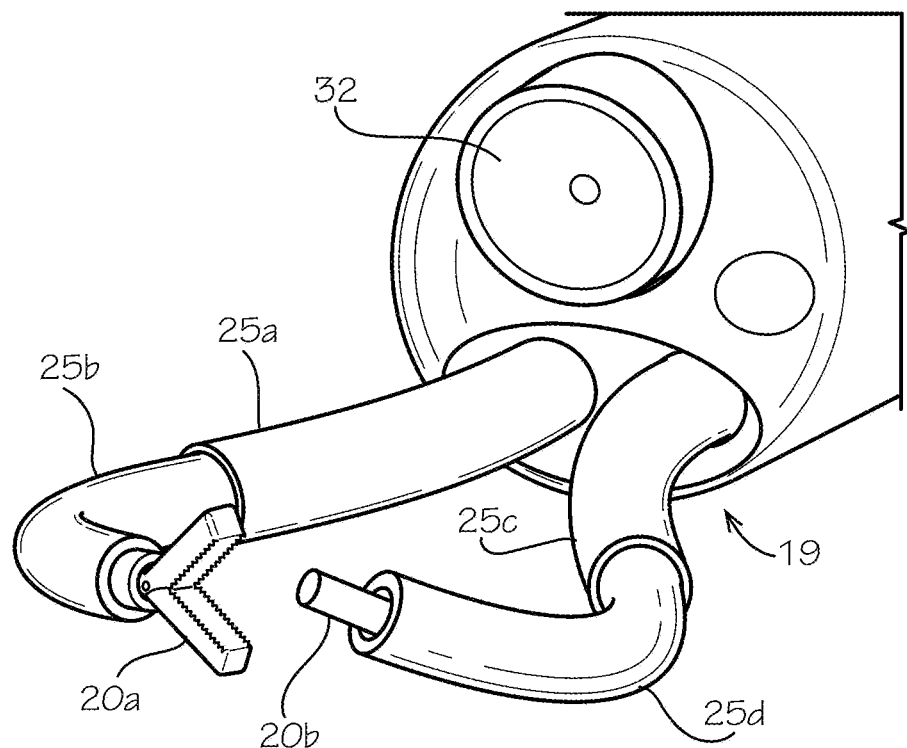
FIG. 3 illustrates a perspective view of a prior art embodiment of an endoscope with separate concentric tube manipulator assemblies protruding from the distal tip.

Referring to FIG. 3, in some embodiments, it is desirable to include two surgical tools 20a, 20b protruding from end opening 19. Each tool includes an end effector that may be positioned using one or more concentric tubes 25a, 25b, 25c, 25d. Such configurations are known in the art for allowing a surgeon to position and steer the end effectors to a desired location at the surgery site. However, such multiple concentric tube configurations are generally fixed and are not insertable through a working channel in an endoscope, resectoscope or trocar due to the relatively large effective diameter of each concentric tube working end caused by the curvature of each tube. As such, conventional concentric tube assemblies for surgical robotics are not amenable to be interchanged by insertion and removal through a small diameter working channel in an endoscope, resectoscope or trocar.

Figure 4:
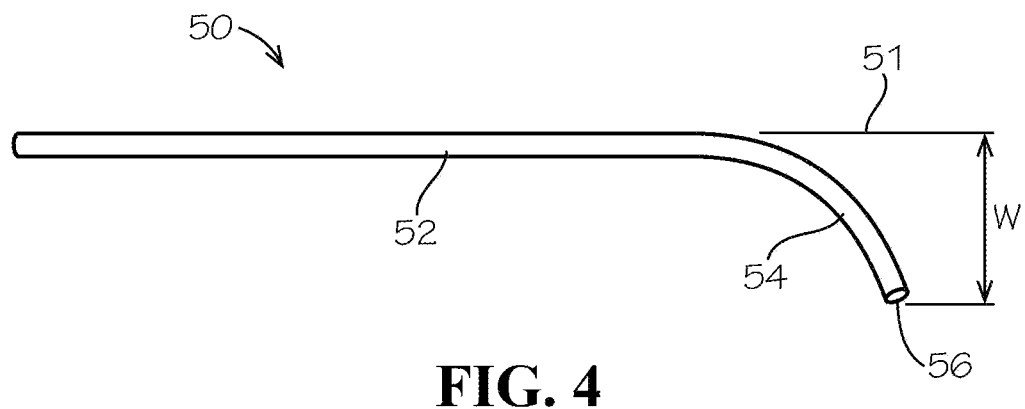
FIG. 4 illustrates a perspective view of an embodiment of a guide tube with a curved distal end.

An example of an elongated tube for guiding a surgical tool through a working channel of an endoscope, resectoscope or trocar is shown in FIG. 4. The various tubes illustrated herein are not drawn to scale, and may include various aspect ratios, lengths, inner diameters, outer diameters, wall thicknesses and curvature profiles not shown. Person of skill in the art will readily understand that the tubes disclosed herein may take many different embodiments in practice. A guide tube 50, or inner tube, is shown in FIG. 4. Guide tube 50 includes a guide tube body 52 and a curved working end 54 at the distal end of the guide tube body 52. Guide tube 50 includes a hollow interior and may comprise any suitable material such as a metal or metal alloy. In some embodiments, guide tube 50 comprises a nickel-titanium, or Nitinol, alloy. Guide tube 50 is generally used to steer a surgical tool to a desired location at a surgical site at the distal tip of an endoscope, resectoscope or trocar. The surgical tool may be axially housed inside the guide tube 50, and the surgical end effector may be deployed or retracted in vivo through the guide tube distal end opening 56.

The curved working end 54 of the guide tube 50 is pre-shaped to have a desired curvature profile. In some embodiments, the curvature profile of the curved working end 54 is optimized to provide maximum steerability of the surgical end effector in the field of view of the optical lens 32.

One drawback of having a curved working end 54 on a guide tube 50 is the curvature profile of the guide tube curved working end 54 causes the guide tube 50 to have an effective outer dimension, or effective diameter, W. In most applications, the guide tube effective diameter W is greater than a corresponding working channel inner diameter on an endoscope, resectoscope or trocar. Thus, it can be difficult or impossible to insert or remove a guide tube 50 with a curved working end 54 axially through the working channel.

Figure 5:
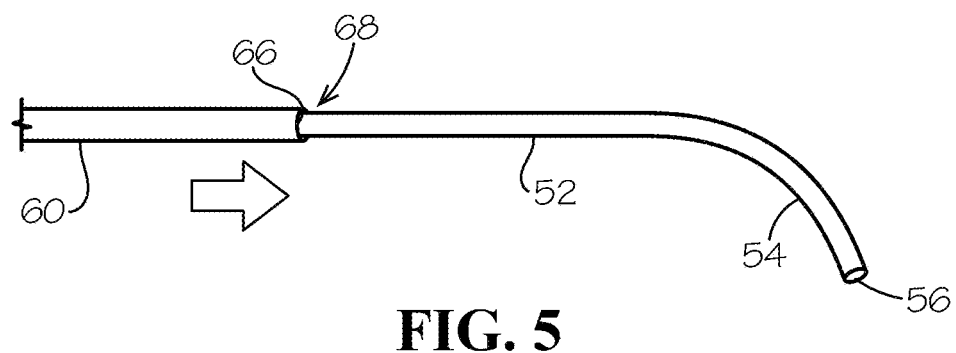
FIG. 5 illustrates a partial perspective view of an embodiment of a guide tube with a distal end being positioned inside a straightening tube.
Figure 6:
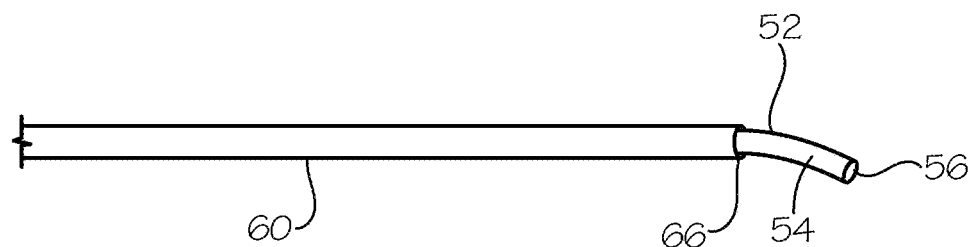
FIG. 6 illustrates a partial perspective view of the embodiment of a guide tube in FIG. 5 positioned inside the straightening tube such that a portion of the curved distal end of the guide tube is received inside and straightened by the straightening tube.
Figure 7:
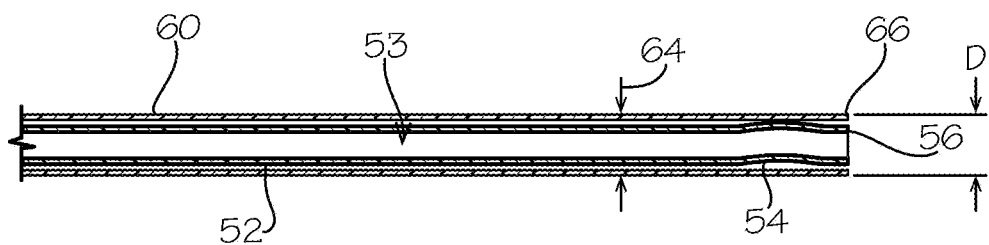
FIG. 7 illustrates a cross-sectional view of an embodiment of a guide tube with a curved distal end housed inside a straightening tube.

As shown in FIGS. 5 to 7, in some embodiments, an outer tube or straightening tube 60 may be positioned over the outside of the guide tube 50. Straightening tube 60 includes a cylindrical tube with a hollow interior. The inner diameter of the straightening tube 60 is slightly larger than the outer diameter of the guide tube 50 such that the guide tube 50 fits closely inside the straightening tube 60 yet is still able to translate axially and rotate relative to the straightening tube 60. As shown in FIG. 5, straightening tube 60 includes a straightening tube distal end 66 and a straightening tube distal end opening 68. The guide tube 50 is received in the straightening tube distal end opening 68. When the curved working end 54 of the guide tube 50 is translated into the straightening tube 60, the curved working end 54 is deflected or strained away from its biased curved position toward the guide tube axis 51. When the curved working end 54 of the guide tube 50 is fully seated inside the straightening tube 60, as shown in FIG. 7, the guide tube distal end opening 56 is axially aligned with the straightening tube distal end 66. In this position, the curved working end 54 is also constrained by the straightening tube such that the curved working end 54 is significantly straightened. In such embodiments, the overall effective outer diameter of the straightening tube distal end 66 and the curved working end 54, D, is substantially equal to the outer diameter of the straightening tube 60.

In some embodiments, the curved working end 54 may impart a force on the straightening tube distal end 66 causing the straightening tube distal end 66 to flex slightly. However, the strain placed on the straightening tube is generally not significant enough to prevent the straightening tube 60 from being able to be inserted through a working channel.

Figure 8:
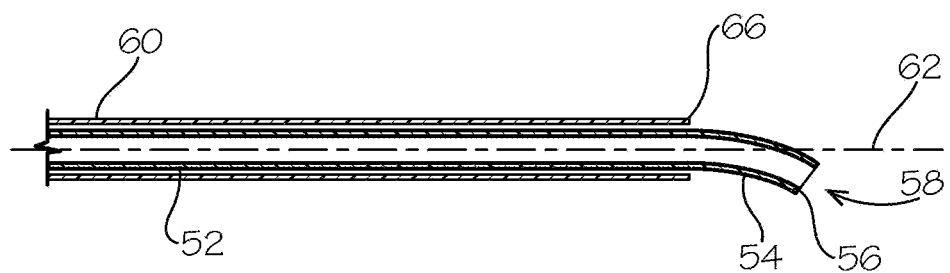
FIG. 8 illustrates a cross-sectional view of an embodiment of a guide tube with a curved distal end partially protruding from the straightening tube.

As shown in FIG. 8, the guide tube 50 may be translated axially inside the straightening tube 60 to expose a portion of the curved working end 54 from the distal end of the straightening tube 66. As the guide tube 50 is axially translated causing the curved working end 54 to protrude out of the straightening tube distal end 66, the curved working end 54 returns to its pre-curved biased position away from the straightening tube axis 62. The orientation of the guide tube distal end opening 58 is controlled by precise translation and rotation of the guide tube 50 and the straightening tube 60.

Figure 9:
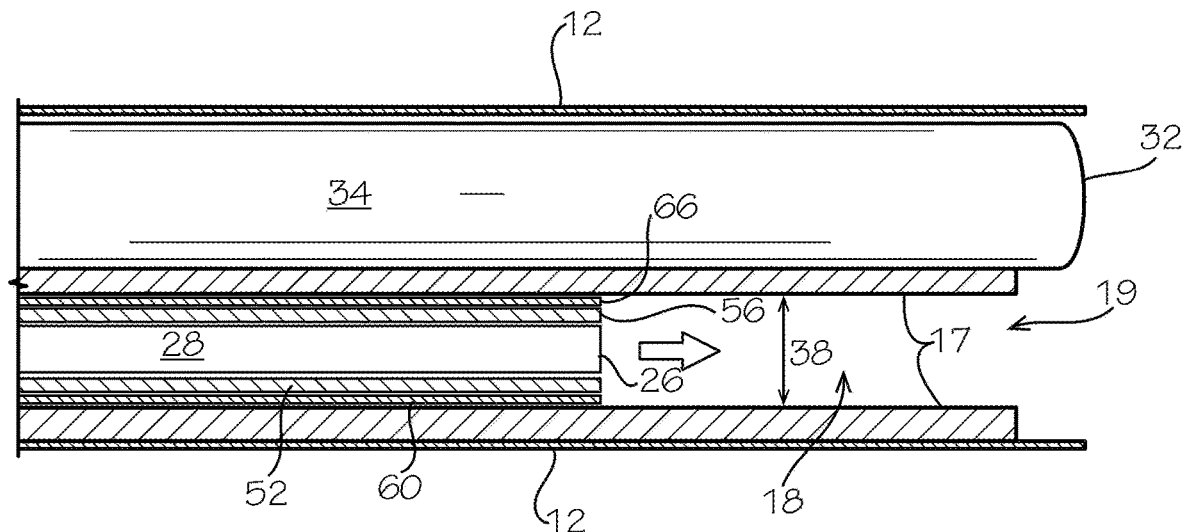
FIG. 9 illustrates a partial cross-sectional view of an embodiment of an endoscope, resectoscope or trocar including a straightening tube, guide tube and surgical tool assembly partially inserted through the working channel.
Figure 10:
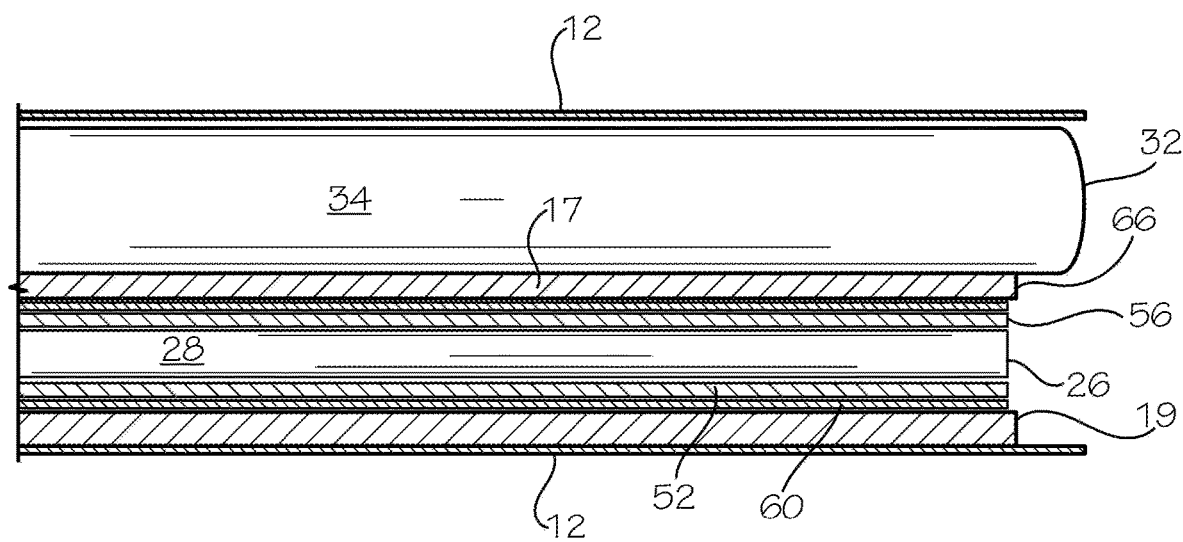
FIG. 10 illustrates a partial cross-sectional view of an embodiment of an endoscope, resectoscope or trocar including a straightening tube, guide tube and surgical tool assembly inserted through the working channel to a ready position.

Referring to FIGS. 9 and 10, guide tube 50 includes a guide tube body 52 and guide tube curved working end 54 housed inside a straightening tube 60. The guide tube and straightening tube assembly 50, 60 together includes a dimensional profile allowing the assembly to be inserted through the working channel 18 defined by working channel inner wall 17. Working channel 18 includes an inner working channel diameter 38 formed in the longitudinal shaft 12 of the endoscope, resectoscope or trocar. Working channel 18 includes a distal end 19 including an opening formed at the distal tip of the working channel. The guide tube and straightening tube assembly 50, 60 may be inserted through the working channel at the same time, as shown in FIG. 9. Additionally, during insertion of the guide tube and straightening tube assembly 50, 60, a surgical tool having a surgical tool shaft 28 and surgical tool distal end 26 may also be housed inside the guide tube 50. During insertion of the guide tube and straightening tube assembly 50, 60, the guide tube distal end 56 and straightening tube distal end 66 are axially aligned with the surgical tool distal end 26 in some applications.

Figure 11:
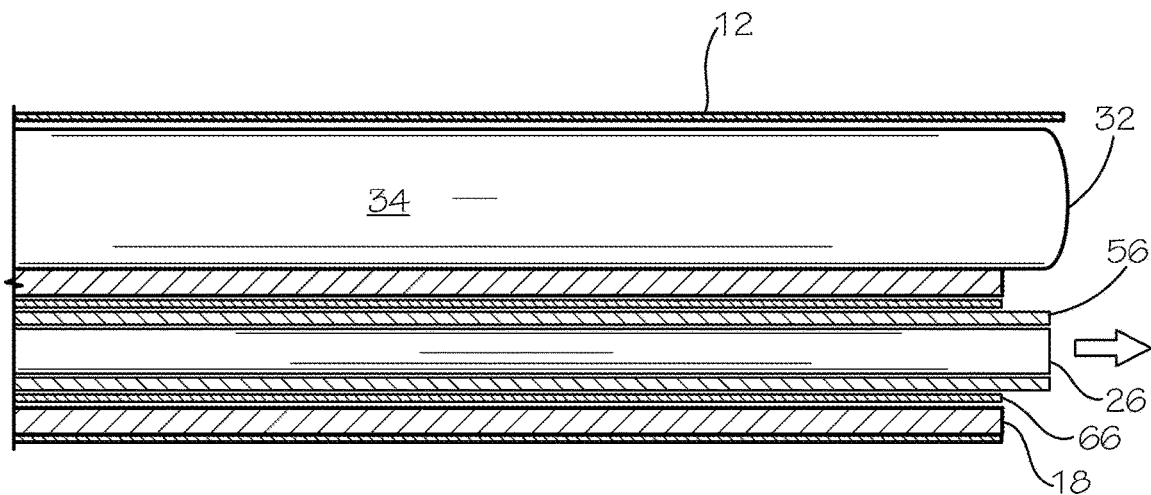
FIG. 11 illustrates a partial cross-sectional view of an embodiment of an endoscope, resectoscope or trocar including a straightening tube, guide tube and surgical tool assembly inserted through the working channel, with the guide tube and surgical tool partially extending from the straightening tube.

As shown in FIG. 10, the guide tube and straightening tube assembly 50, 60 is inserted through the working channel 18 until the guide tube distal end 56 and straightening tube distal end 66 are axially aligned with the working channel distal end 19. In this position, the surgical tool distal end 26 is also axially aligned with the guide tube distal end 56 and straightening tube distal end 66. At this ready position, forward translation of the straightening tube 60 is limited; however, the guide tube 50 and surgical tool 20 may be translated in tandem or independently axially relative to the stationary straightening tube 60 as shown in FIG. 11. The forward translation of the guide tube distal end 56 and straightening tube distal end 66 are controlled by a manual actuator or an electro-mechanical transmission linkage coupled to the tubes. As the guide tube distal end 56 and straightening tube distal end 66 advance axially out of the opening at the distal end of the straightening tube, the curved working end 54 of the guide tube 50 returns to its pre-shaped curvature in its preferred biased position. In some applications, the straightening tube distal end 66 may extend beyond the working channel distal end 19 into the surgical field to further effect manipulation of the guide tube and surgical tool.

The guide tube angle 53 is a function of the axial position of the guide tube curved working end 54 relative to the straightening tube 60. As the guide tube 50 advances forward away from straightening tube 60, the guide tube angle 53 increases until the curved working end 54 assumes its fully biased curvature profile. When the guide tube 50 is retracted relative to the straightening tube 60, the guide tube angle 53 decreases toward a limit of zero in some embodiments as the curved working end 54 is drawn into the straightening tube 60.

Figure 12:
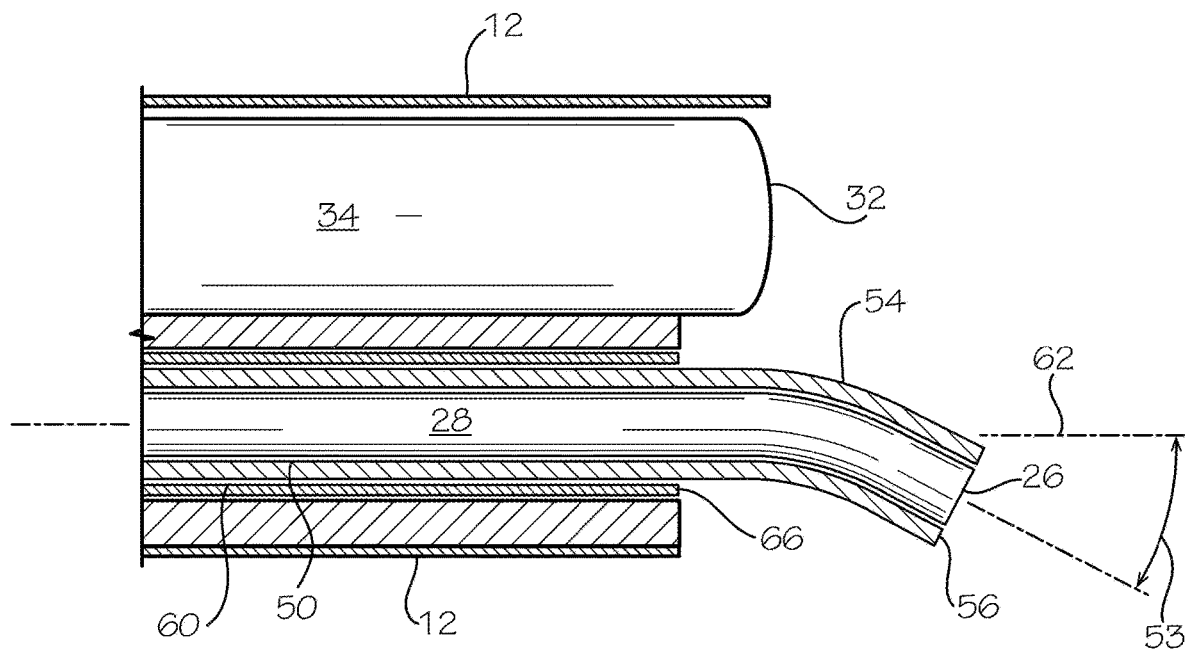
FIG. 12 illustrates a partial cross-sectional view of an embodiment of an endoscope, resectoscope or trocar including a straightening tube, guide tube and surgical tool assembly inserted through the working channel, with the guide tube and surgical tool partially extending from the straightening tube.
Figure 13:
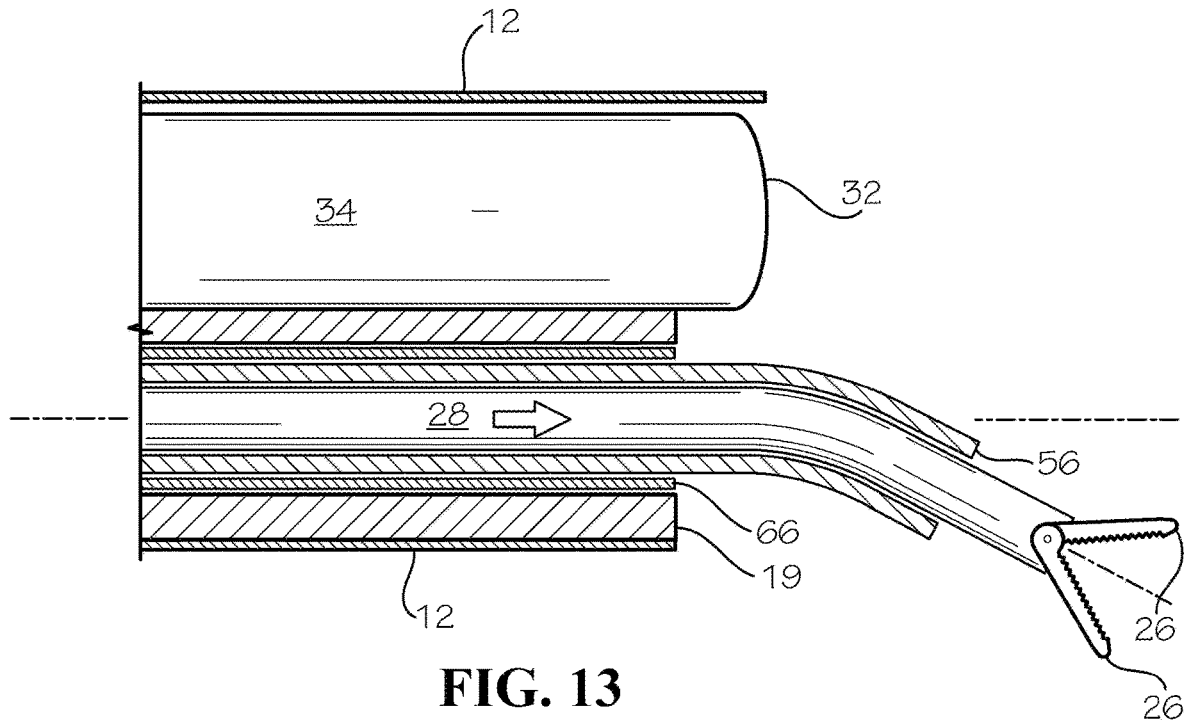
FIG. 13 illustrates a partial cross-sectional view of an embodiment of an endoscope, resectoscope or trocar including a straightening tube, guide tube and surgical tool assembly inserted through the working channel, with the guide tube extending from the straightening tube, and the surgical tool extending from the guide tube.

Once the guide tube 50 is translated and rotated into a desired position, for example as shown in FIG. 12, the surgical tool 20 may be deployed by axially translating the surgical tool shaft 28 through the guide tube 50. Such translation of the surgical tool shaft 28 causes the surgical tool distal end 26 to protrude beyond the guide tube distal end 56, as shown in FIG. 13. In further embodiments, the surgical tool distal end 26 is fixed to the guide tube distal end 56 such that the surgical tool distal end 26 is not translatable axially relative to the guide tube 50.

Figure 14:
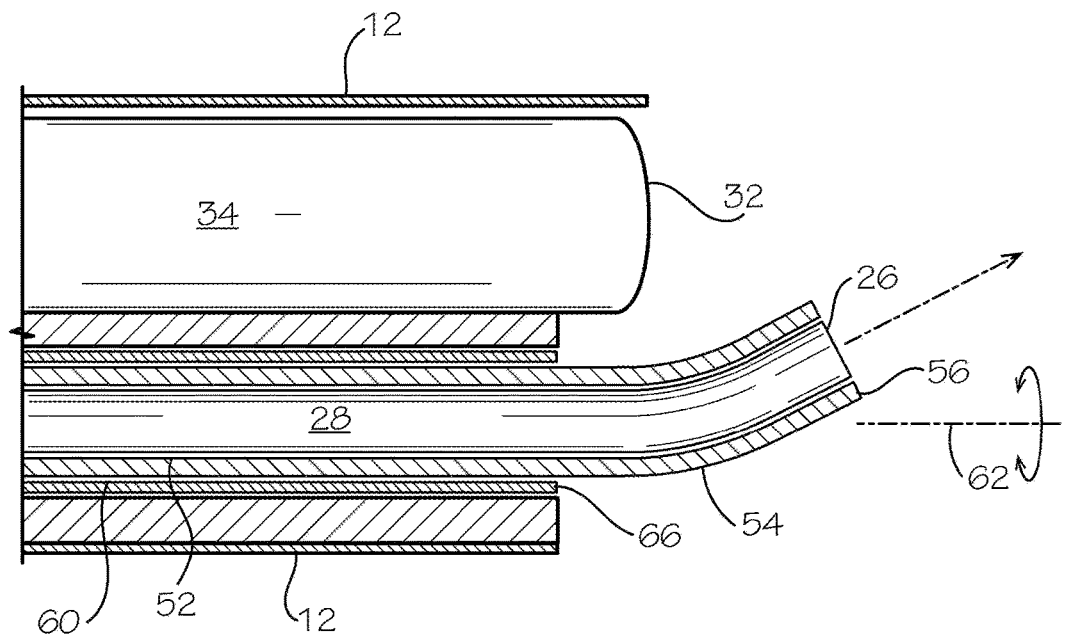
FIG. 14 illustrates a partial cross-sectional view of an embodiment of an endoscope, resectoscope or trocar including a straightening tube, guide tube and surgical tool assembly inserted through the working channel, with the guide tube and surgical tool partially extending from the straightening tube and rotated about the working channel axis.
Figure 15:
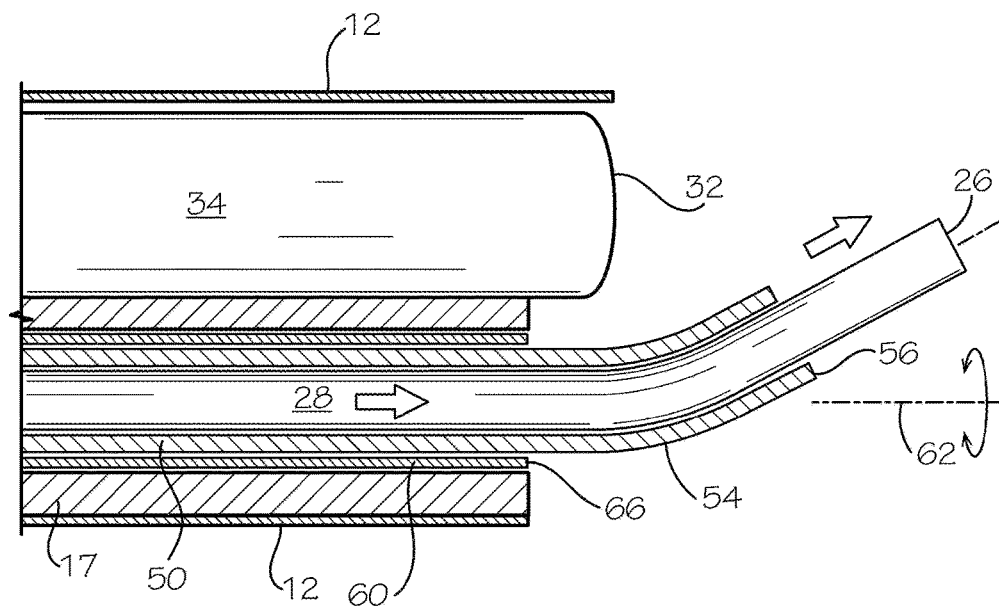
FIG. 15 illustrates a partial cross-sectional view of an embodiment of an endoscope, resectoscope or trocar including a straightening tube, guide tube and surgical tool assembly inserted through the working channel, with the guide tube partially extending from the straightening tube and rotated about the working channel axis and the surgical tool extending from the guide tube.
Figure 16:
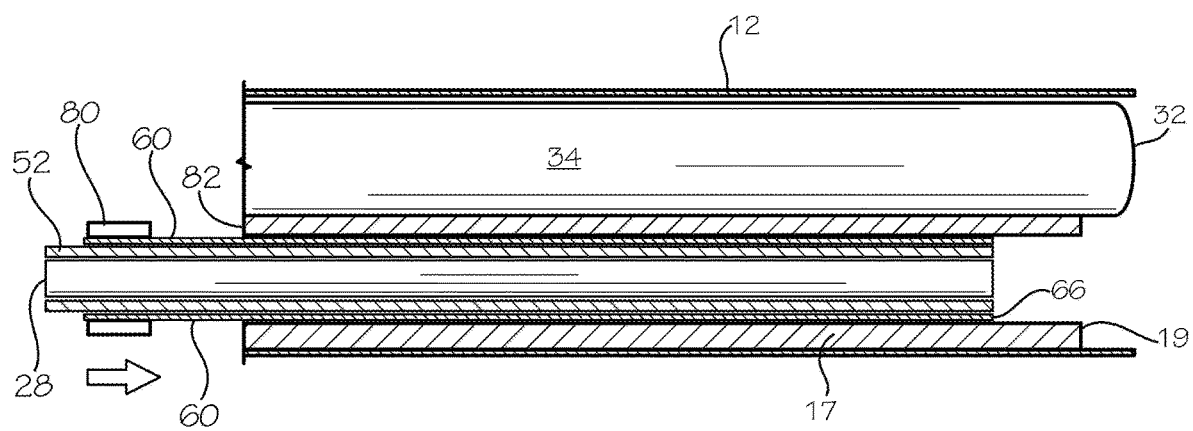
FIG. 16 illustrates a partial cross-sectional view of an embodiment of an endoscope, resectoscope or trocar including a straightening tube, guide tube and surgical tool assembly partially inserted through the working channel with an axial stop positioned to limit translation of the straightening tube to a desired position in the working channel.

As shown in FIGS. 14-15, the guide tube may be subsequently rotated and/or translated while also moving the axial position of the surgical tool shaft 28 to maneuver the surgical tool distal end 26 to a desired location. The ability to rotate and translate guide tube 50 relative to straightening tube 60, combined with the ability to translate surgical tool shaft 28 relative to guide tube 50, provides a technical solution with multiple degrees of freedom for enhancing steerability of the surgical end effector inside the field of view of the lens 32.

Figure 17:
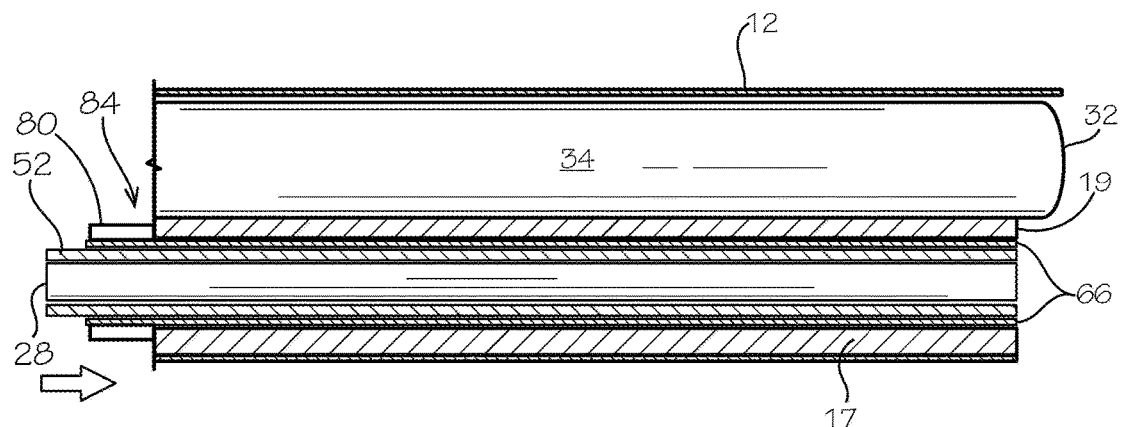
FIG. 17 illustrates a partial cross-sectional view of the embodiment of an endoscope, resectoscope or trocar of FIG. 16 including a straightening tube, guide tube and surgical tool assembly inserted through the working channel with the axial stop limiting translation of the straightening tube to a desired position in the working channel.
Figure 18:
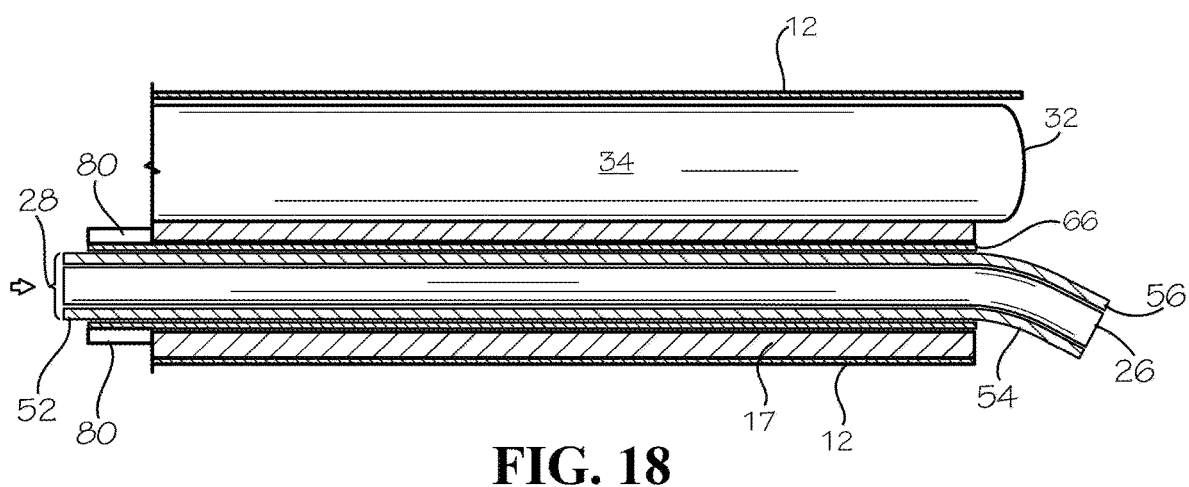
FIG. 18 illustrates a partial cross-sectional view of the embodiment of an endoscope, resectoscope or trocar of FIGS. 16 and 17 including a straightening tube, guide tube and surgical tool assembly inserted through the working channel with the axial stop limiting translation of the straightening tube to a desired position in the working channel and the guide tube and surgical tool extending from the straightening tube.
Figure 19:
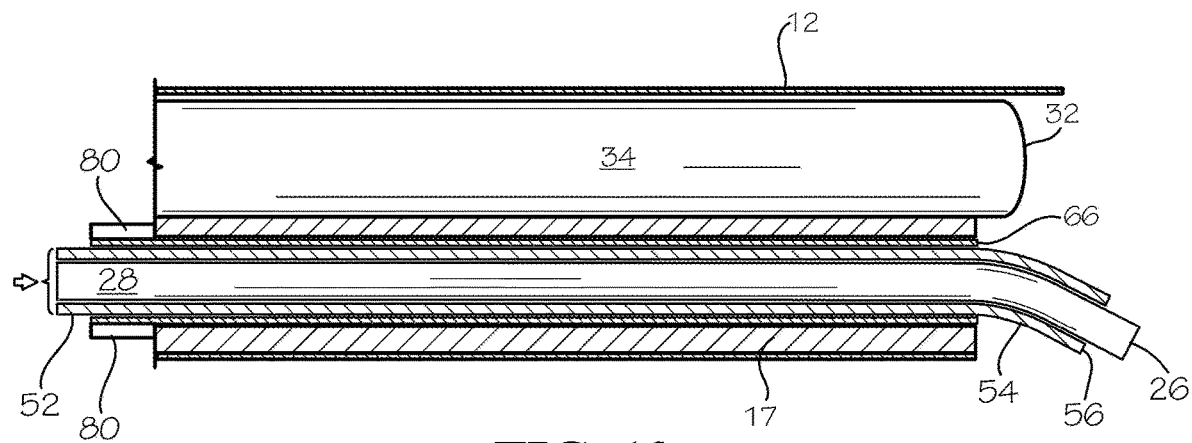
FIG. 19 illustrates a partial cross-sectional view of the embodiment of an endoscope, resectoscope or trocar of FIGS. 16, 17 and 18 including a straightening tube, guide tube and surgical tool assembly inserted through the working channel with the axial stop limiting translation of the straightening tube to a desired position in the working channel, the guide tube extending from the straightening tube, and the surgical tool extending from the guide tube.

Referring to FIGS. 16-19, in some applications it is desirable to stop the axial translation of the guide tube distal end 56 and straightening tube distal end 66 at the distal end of the working channel. An axial stop 80 may be disposed on or linked to the straightening tube 60. Axial stop 80 can take many forms, including an annular flange protruding radially from the proximal end of straightening tube 60. Axial stop 80 interferes with a corresponding mechanical structure on the apparatus when the straightening tube distal end 66 is axially aligned with the distal end of the working channel, as shown in FIG. 17. The structure engaging axial stop 80 to limit forward travel of straightening tube 60 may include a shoulder on the proximal end of the working channel 82 in some embodiments. When the axial stop 80 approaches and contacts the working channel proximal end at a contact location 84, forward travel of the straightening tube 60 is stopped. From the position where the straightening tube 60 is limited in forward travel by axial stop 80, guide tube proximal end 52 may be freely advanced forward relative to stationary straightening tube 60, thereby allowing the curved working end 54 and surgical tool distal end 26 to advance out of the straightening tube distal end 66 together as shown in FIG. 18. Once the guide tube curved working end 54 reaches a desired orientation, the surgical tool distal end 26 may be deployed from the guide tube distal end 56 by translating the surgical tool shaft 28 forward. Likewise, the surgical tool distal end 26 may be retracted relative to the guide tube 54 by reversing the translation direction of the surgical tool shaft 28.

Figure 20:
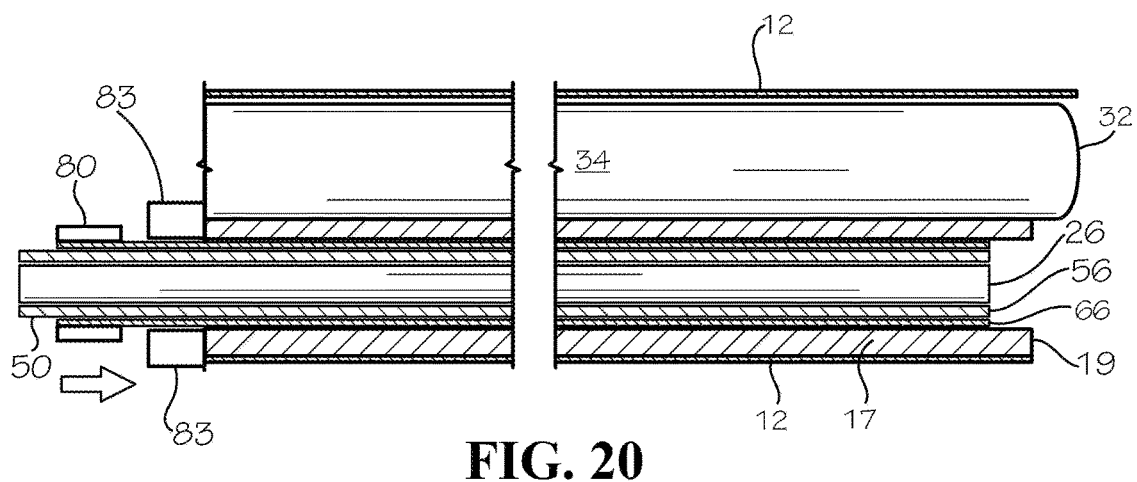
FIG. 20 illustrates a partial cross-sectional view of an alternative embodiment of an endoscope, resectoscope or trocar including a straightening tube, guide tube and surgical tool assembly partially inserted through the working channel with an axial stop positioned to limit translation of the straightening tube to a desired position in the working channel.
Figure 21:
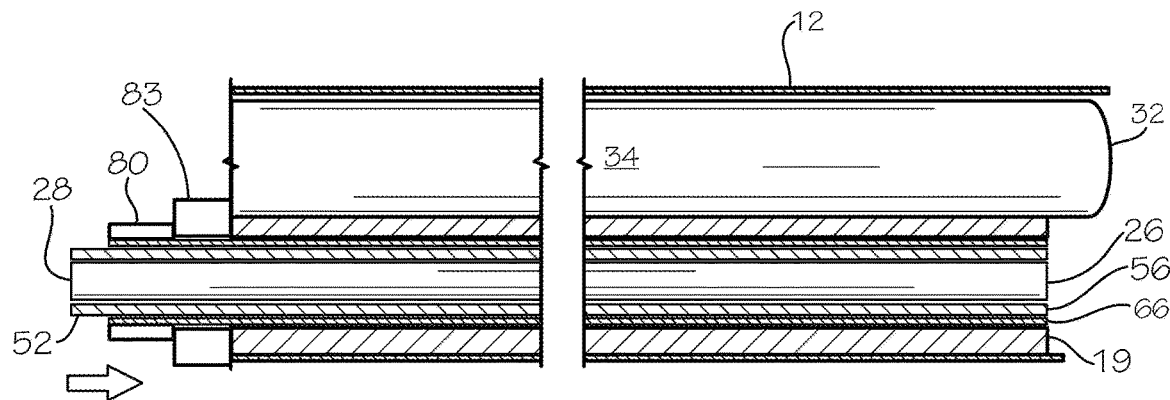
FIG. 21 illustrates a partial cross-sectional view of the embodiment of an endoscope, resectoscope or trocar of FIG. 20 including a straightening tube, guide tube and surgical tool assembly inserted through the working channel with the axial stop limiting translation of the straightening tube to a desired position in the working channel.

In further embodiments, as shown in FIGS. 20 and 21, the axial stop 80 on straightening tube 60 engages a structure 83 outside of the working channel to stop the forward axial translation of the guide tube 50 and straightening tube 60. When the axial stop 80 contacts structure 83, the forward translation of straightening tube 60 is stopped. In some embodiments, the relative locations of axial stop 80 and structure 83 are positioned such that when contact is made, the straightening tube distal end 66 and the guide tube distal end 56 are axially aligned with the working channel distal end 19. From this position, the guide tube 50 may be translated forward to extend the curved working end of the guide tube and to deploy the surgical tool distal end 26.

In some applications, during a surgical procedure, it is desirable to remove a surgical tool from the endoscope, resectoscope or trocar through the working channel while the device is positioned inside a patient's body without removing the endoscope, resectoscope or trocar. For example, a different surgical tool may be needed for a different stage of an operation. To accommodate this, in some embodiments the present invention provides a concentric tube robot apparatus 90 including a transmission 92 coupled to a tube array. The tube array includes a guide tube 50 with a curved working end 54 housed inside a straightening tube 60. The guide tube 50 is straightened at least partially by the straightening tube 60 so that the tube array may be axially inserted into or removed from a working channel on an endoscope, resectoscope or trocar.

Concentric tube robot apparatus 90 also includes a surgical tool with a shaft and an end effector housed within the guide tube 50. The guide tube 50 may be axially translated and rotated relative to the straightening tube 60. The axial translation and rotation of the guide tube 50 is driven by a guide tube translation drive 94a and a guide tube rotation drive 96a. Each of the guide tube translation drive 94a and guide tube rotation drive 96a are mechanically coupled to guide tube 50 inside transmission 92. The guide tube translation drive 94a controls axial translation of guide tube 50 relative to straightening tube 60. The guide tube rotation drive 96a controls angular rotation of guide tube 50 relative to straightening tube 60. Each guide tube drive may be driven manually or using an electro-mechanical actuator such as a gear box or motor.

Figure 22:
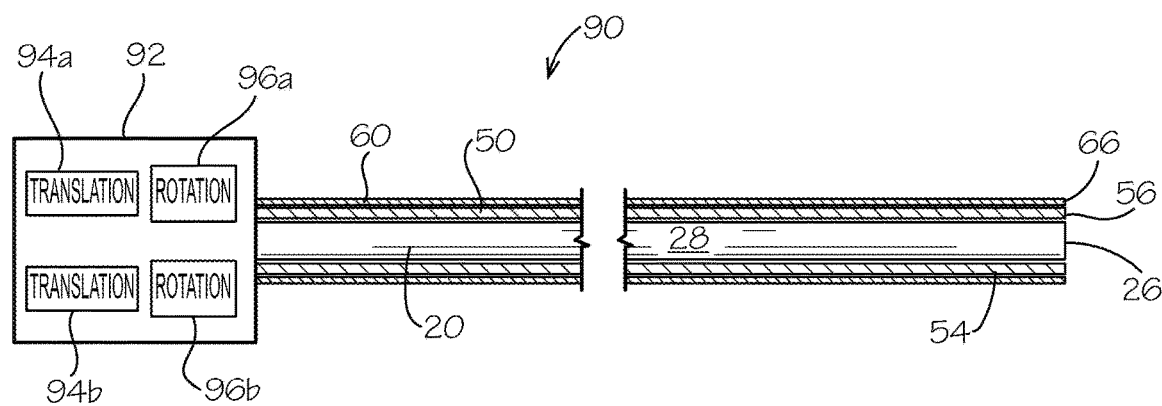
FIG. 22 illustrates a partial cross-sectional schematic view of an embodiment of a robotic assembly with a surgical tool, a guide tube and a straightening tube coupled to a transmission including guide tube translation and rotation and surgical tool translation and rotation drives.
Figure 23:
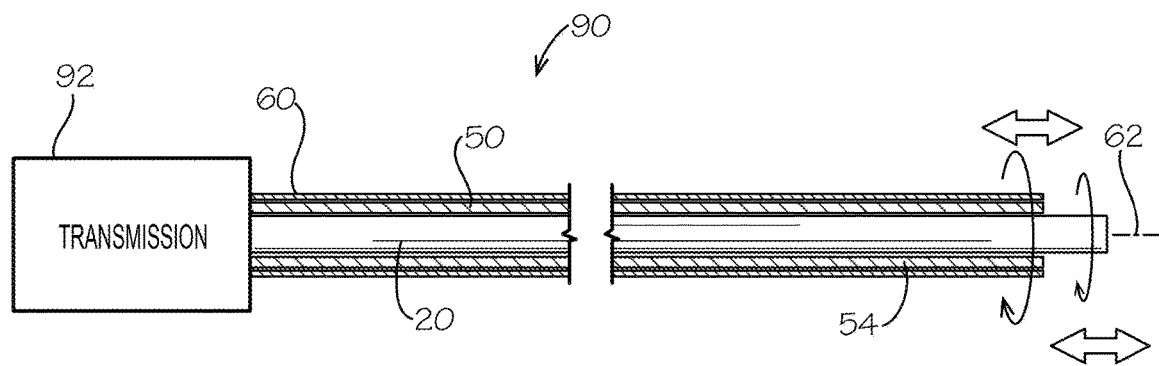
FIG. 23 illustrates a partial cross-sectional view of an embodiment of a tube array with a transmission for insertion into a working channel.

Also shown in FIGS. 22 and 23, in some embodiments, transmission 92 also includes a surgical tool translation drive 94b and a surgical tool rotation drive 96b. The axial translation and rotation of the surgical tool 20 relative to the guide tube 50 is controlled by the translation and rotation drives 94b, 96b, respectively.

Figure 24:
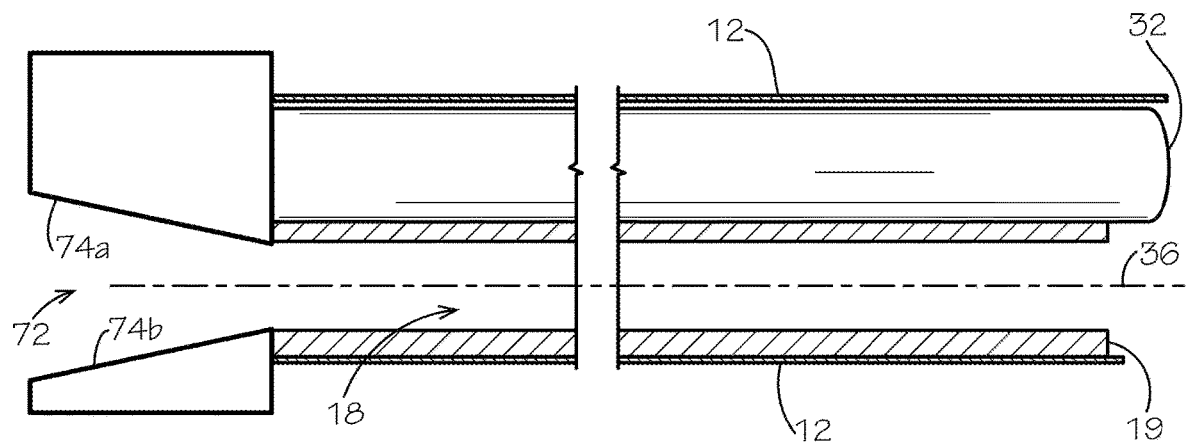
FIG. 24 illustrates a partial cross-sectional view of an embodiment of an endoscope with an insertion port at the proximal end of the working channel.

When it is desired to change a surgical tool, a removable concentric tube robot apparatus 90, forming a removable cartridge, may be removed as a single unit from the device by sliding the tube array out of the working channel. During removal, the straightening tube 60 is operable to constrain the curved working end of the guide tube enough to facilitate removal of the tube array through the longitudinal working channel. A second concentric tube robot apparatus may be inserted through an insertion port, 72, shown in FIG. 24, at the proximal end of the endoscope, resectoscope or trocar. The insertion port 72 provides an opening for insertion of the tube array and surgical tool assembly on the concentric tube robot apparatus 90. In some embodiments, insertion port 72 includes a ramped surface including first and second ramps 74a, 74b. In other embodiments, insertion port 72 includes an axisymmetric funnel shaped to feed the distal tip of the tube array into the proper location along the working channel longitudinal axis 36 for insertion into and through the working channel 18.

Figure 25:
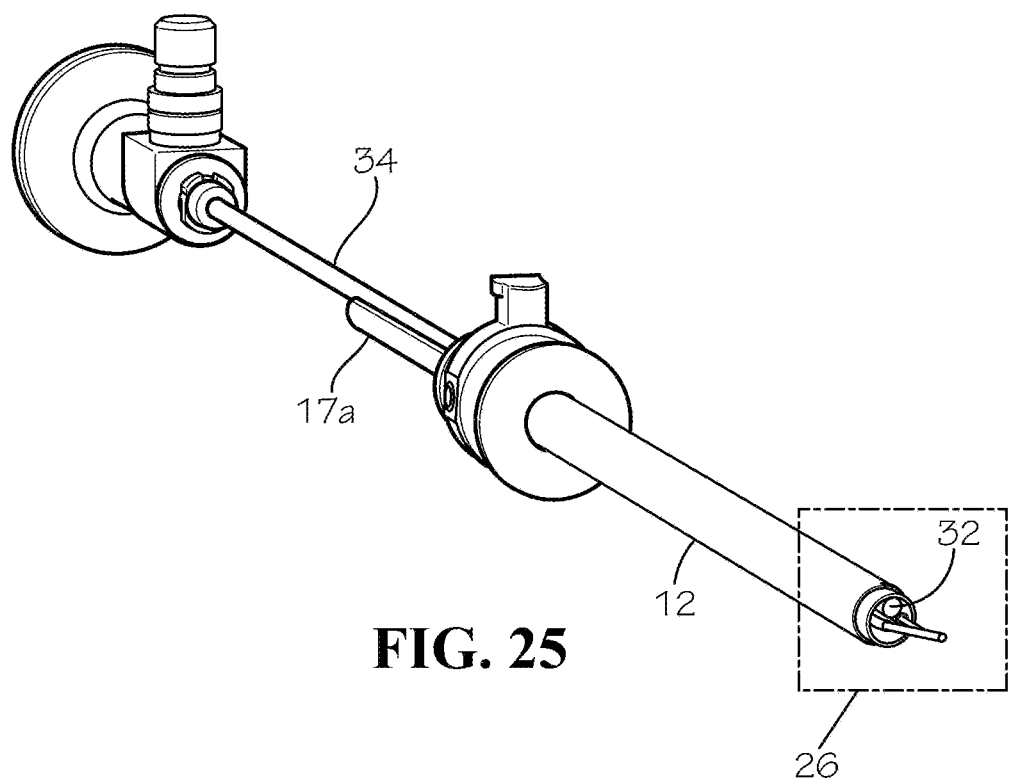
FIG. 25 illustrates a perspective view of an embodiment of a resectoscope including an optical lens partially inserted into the shaft.
Figure 26:
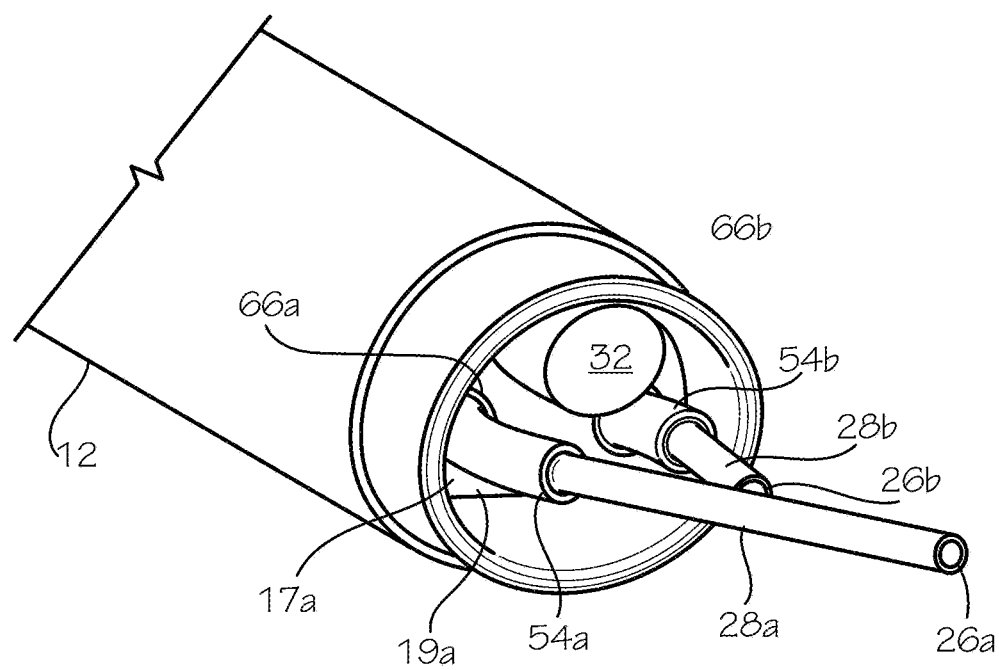
FIG. 26 is a detail perspective view of Section 26 from FIG. 25.

Referring to FIGS. 25 and 26, in additional embodiments, an endoscope, resectoscope or trocar includes a shaft 12 with a hollow interior. The shaft 12 receives an optic element 34 such as a rod lens or optical fiber that extends longitudinally through the shaft 12. Alternatively, optic element 34 can include a cable to a chip-tip style camera positioned on the distal end of the working channel including lens 32. A working channel may be defined through the interior region on the shaft below the optical element 34 in some embodiments. In other embodiments, the working channel is defined in a cannula, or working channel insert 17a positioned inside the hollow interior of shaft 12. Additionally, as shown in FIG. 26, in some applications it is desirable to include two surgical tools with surgical tool distal ends 26a, 26b positioned in the field of view of lens 32. Each surgical tool is housed within a corresponding guide tube. First surgical tool distal end 26a and tool shaft 28a extend from first guide tube curved working end 54a. Second surgical tool distal end 26b and tool shaft 28b extend from second guide tube curved working end 54b. As shown in FIG. 26, first and second tube arrays are positioned in separate working channels formed in a working channel insert 17a having a working channel insert distal end 19a. The first tube array includes a straightening tube with a first straightening tube distal end 66a axially aligned with the distal end 19a of the working channel insert 17a. Similarly, the second tube array includes a straightening tube with a second straightening tube distal end 66b axially aligned with the distal end 19a of the working channel insert 17a. As such, the first and second straightening tube distal ends 66a, 66b do not extend from the working channel openings at the distal end of the working channel insert. A first guide tube curved working end 54a protrudes from the first straightening tube distal end 66a, and a second guide tube curved working end 54b protrudes from the second straightening tube distal end 66b. Each guide tube and straightening tube may be rotated and translated. In some embodiments, each guide tube and straightening tube may be rotated together. A first surgical tool distal end 26a may be translated in and out of first guide tube curved working end 54a, and second surgical tool distal end 26b may be translated in and out of second guide tube curved working end 54b.

Figure 27:
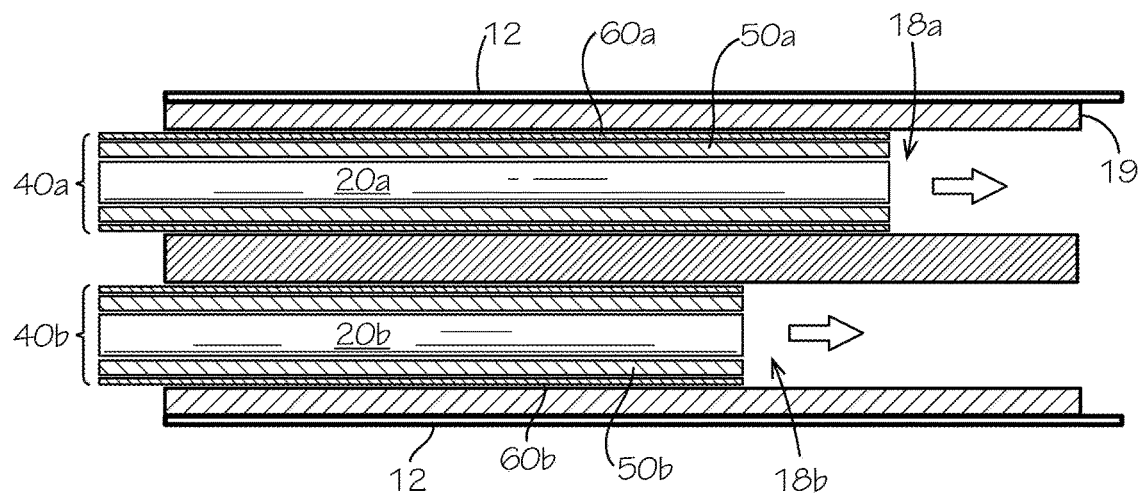
FIG. 27 illustrates a partial cross-sectional view of an embodiment of an endoscope, resectoscope or trocar including first and second working channels and tube arrays.
Figure 28:
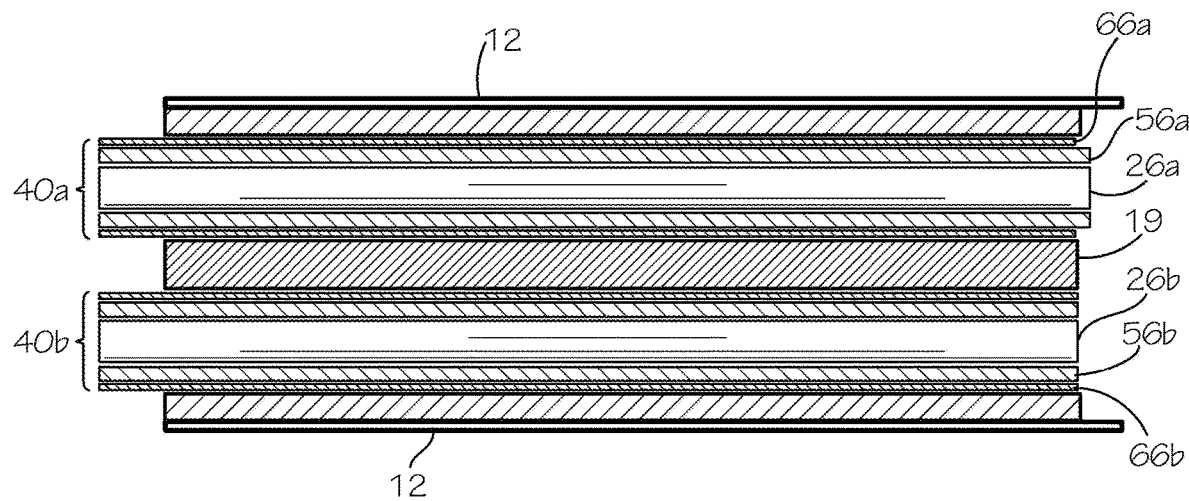
FIG. 28 illustrates a partial cross-sectional view of an embodiment of an endoscope, resectoscope or trocar including first and second working channels and tube arrays.

A partial cross-sectional view of an embodiment of a shaft with first and second tube arrays is shown in FIGS. 27 and 28. Referring to FIG. 27, a first tube array 40a is inserted in a first working channel 18a, and a second tube array 40b is inserted in a second working channel 18b. The first and second tube arrays 40a, 40b each include a straightening tube 60a, 60b, a guide tube 50a, 50b and a surgical tool 20a, 20b, respectively. First and second tube arrays 40a, 40b may be inserted or removed independently of the other. In some embodiments, the first straightening tube 60a of first tube array 40a may be inserted to a position where the first straightening tube distal end 66a is aligned with the working channel distal end 19. From this position, the first guide tube distal end 56a and first surgical tool distal end 26a may be translated beyond the first straightening tube distal end 66a to deploy the first curved working end and first surgical tool end effector. Similarly, the second straightening tube 60b of the second tube array 40b may be inserted to a position where the second straightening tube distal end 66b is aligned with the working channel distal end. From this position, the second guide tube distal end 56b and second surgical tool distal end 26b may be translated beyond the second straightening tube distal end 66b to deploy the second curved working end and second surgical tool end effector.

Figure 29:
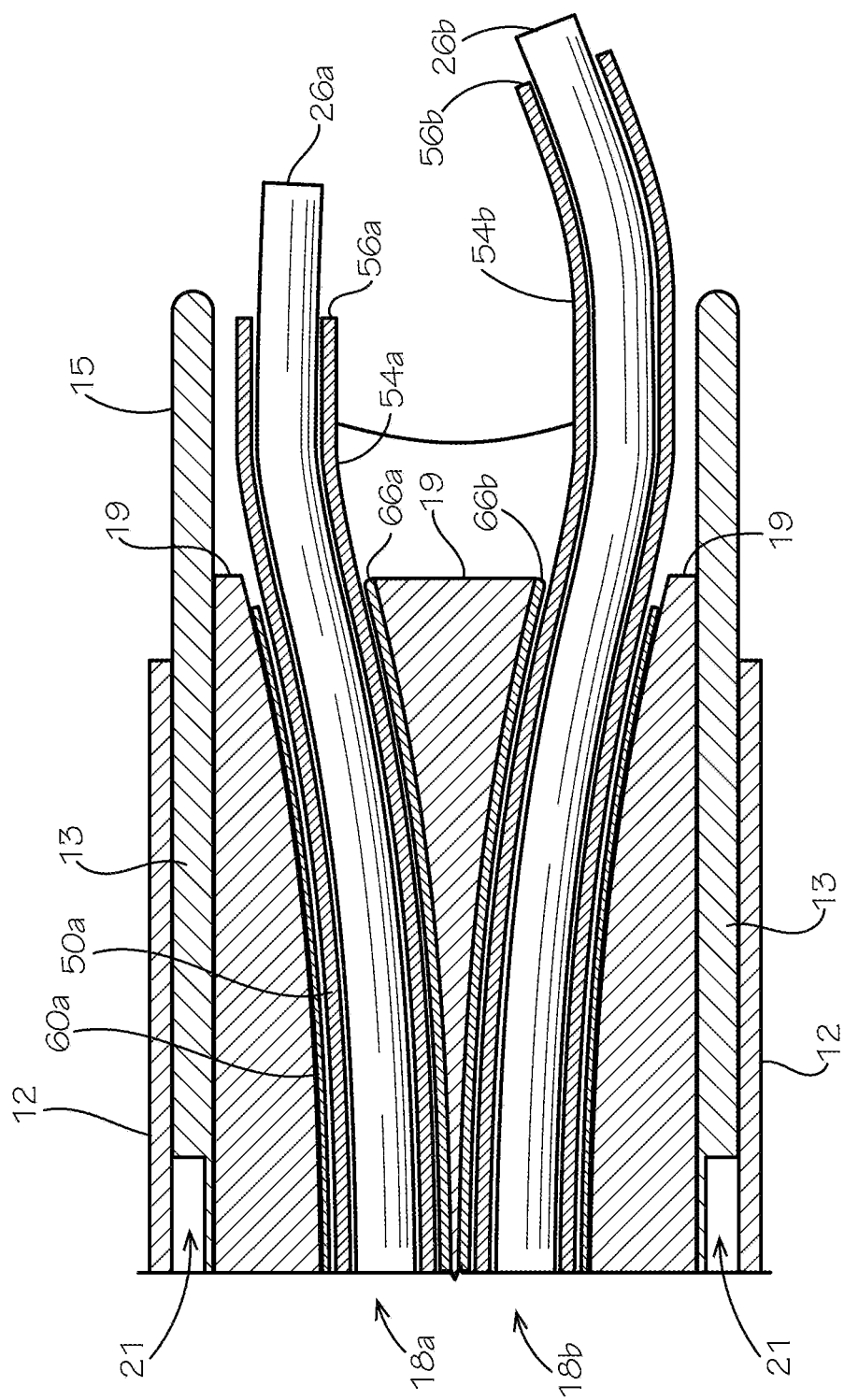
FIG. 29 illustrates a partial cross-sectional view of an embodiment of surgical robot assembly including first and second tube arrays positioned in first and second working channels, each having a curved working end partially extended from its corresponding straightening tube.

Referring further to FIG. 29, in some embodiments a device for performing minimally invasive surgery includes a shaft 12 including shaft liner 13. A plenum 21 is defined between the shaft 12 and the shaft liner 13. In some embodiments, plenum 21 is used as a duct for suction or irrigation. First and second working channels 18a, 18b are defined inside the shaft. A first tube array is inserted in first working channel 18a, and a second tube array is inserted in second working channel 18b. The first tube array includes a first straightening tube 60a and a first guide tube 50a positioned at least partially inside the first straightening tube. The first guide tube includes a first curved working end 54a that is both axially translatable and angularly rotatable relative to the first straightening tube 60a. First guide tube 50a provides a guide to steer the positioning of first surgical tool distal end 26a. Depending on the axial position and angular position of the first guide tube 50a, first surgical tool distal end 26a may be repositioned with precision in three-dimensional space.

The second tube array includes a second straightening tube 60b and a second guide tube 50b positioned at least partially inside the second straightening tube. The second guide tube includes a second curved working end 54b that is both axially translatable and angularly rotatable. Second guide tube 50b provides a guide to steer the positioning of second surgical tool distal end 26b. Depending on the axial position and angular position of the second guide tube 50b, second surgical tool distal end 26b may be repositioned with precision in three-dimensional space.

As shown in FIG. 29, in some embodiments, first and second straightening tube distal ends 66a, 66b do not extend beyond the distal end 19 of first and second working channels. In some other embodiments, first and second straightening tube distal ends 66a, 66b extend slightly beyond the distal end 19 of first and second working channels, but do not extend beyond the distal end of hood 15.

In further embodiments, the present invention includes a method of performing a surgical procedure, including the steps of (a) providing a concentric tube robot including a guide tube with a curved tip and a straightening tube; (b) positioning the curved tip of the guide tube inside the straightening tube; (c) inserting the guide tube and straightening tube together into a working channel on an endoscope shaft; (d) translating the guide tube relative to the straightening tube to deploy the curved working end of the guide tube; and (e) translating a surgical tool through the guide tube curved working end to a surgical site. The method further includes the steps of rotating the guide tube relative to the straightening tube to reposition the surgical tool. In some embodiments, the method further includes a step of retracting the curved working end of the guide tube into the straightening tube and removing the tube assembly from the working channel.

Thus, although there have been described herein particular embodiments of the present invention of new and useful devices and methods for robotic surgery, it is not intended that such references be construed as limitations upon the scope of this invention except as set forth in the following claims.

What is claimed is:

1. A method, comprising:
    a) providing a concentric tube robot including a straightening tube and a guide tube, the guide tube including a curved working end biased away from a longitudinal axis of the guide tube;
    b) positioning the curved working end of the guide tube inside the straightening tube and mechanically constraining the curved working end of the guide tube toward a longitudinal axis of the straightening tube; and
    c) inserting the guide tube and straightening tube into a working channel on an endoscope while the curved working end of the guide tube is mechanically constrained inside the straightening tube.

2. The method of claim 1, further comprising translating the guide tube axially relative to the straightening tube and deploying the curved working end of the guide tube from the straightening tube.

3. The method of claim 2, further comprising rotating the guide tube relative to the working channel.

4. The method of claim 2, further comprising delivering a surgical tool axially through the guide tube such that the surgical tool extends through the curved working end of the guide tube.

5. The method of claim 4, wherein the surgical tool comprises forceps.

6. The method of claim 4, further comprising rotating the guide tube relative to the working channel to reposition the surgical tool.

7. The method of claim 6, further comprising retracting the curved working end of the guide tube into the straightening tube and mechanically constraining the curved working end of the guide tube toward a longitudinal axis of the straightening tube.

8. The method of claim 7, further comprising retracting the guide tube and straightening tube from the working channel while the curved working end of the guide tube is mechanically constrained inside the straightening tube.

* * * * *